(12) United States Patent
Emadi et al.

(10) Patent No.: US 9,381,215 B2
(45) Date of Patent: Jul. 5, 2016

(54) COMPOSITIONS AND METHODS FOR THE TREATMENT OF CANCERS

(71) Applicants: Ashkan Emadi, Clarksville, MD (US); Rena Lapidus, Baltimore, MD (US); Mariola Sadowska, Baltimore, MD (US); Brandon Carter-Cooper, Manchester, MD (US); Edward Sausville, Edgewater, MD (US)

(72) Inventors: Ashkan Emadi, Clarksville, MD (US); Rena Lapidus, Baltimore, MD (US); Mariola Sadowska, Baltimore, MD (US); Brandon Carter-Cooper, Manchester, MD (US); Edward Sausville, Edgewater, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/624,325

(22) Filed: Feb. 17, 2015

(65) Prior Publication Data

US 2015/0231176 A1     Aug. 20, 2015

Related U.S. Application Data

(60) Provisional application No. 61/940,526, filed on Feb. 17, 2014.

(51) Int. Cl.
*A61K 33/36*     (2006.01)
*A61K 31/19*     (2006.01)

(52) U.S. Cl.
CPC ............... *A61K 33/36* (2013.01); *A61K 31/19* (2013.01)

(58) Field of Classification Search
None
See application file for complete search history.

(56) References Cited

PUBLICATIONS

Sun et al. Targeting metabolism with arsenci trioxide and dichloroacetate in breast cancer cells, Molecular Cancer 2011, 10:142.*
Au et al. Arsenic trioxide: safety issues and their management, Acta Pharmacol Sin Mar. 2008; 29(3):296-304.*
Emadi et al. Synergistic Antileukemic Effect of Sequential Administration of Dichloroacetate combined with Arsenic Trioxide in Primary Blasts from Patients with Acute Myeloid Leukemia and FLT3-ITD AML cell lines, Blood, vol. 122, Issue 21, p. 3955, Nov. 15, 2013.*
Mikkael A. Sekeres, Boulevard of Broken Dreams: Drug Approval for Older Adults With Acute Myeloid Leukemia, Journal of Clinical Oncology, Nov. 20, 2012, 30(33):4061-4063.
Ashkan Emadi, Arsenic Trioxide—An Old Drug Rediscovered, Blood Rev. 2010 ; 24(4-5):191-199. doi:10.1016/j.blre.2010.04.001.

* cited by examiner

*Primary Examiner* — Robert A Wax
*Assistant Examiner* — Melissa Mercier
(74) *Attorney, Agent, or Firm* — Benjamin Aaron Adler

(57) ABSTRACT

The present invention provides a formulation comprising dichloroacetate and arsenic trioxide. The present invention also provides a method of treating cancer by administering a therapeutically effective amount of dichloroacetate and arsenic trioxide.

14 Claims, 15 Drawing Sheets

COMPOSITIONS AND METHODS FOR THE TREATMENT OF CANCERS

CROSS-REFERENCE TO RELATED APPLICATIONS

This is a non-provisional application which claims benefit of priority under 35 U.S.C. §119(e) of provisional application U.S. Ser. No. 61/940,526, filed Feb. 17, 2014, now abandoned, the entirety of which is hereby incorporated by reference.

BACKGROUND OF THE INVENTION

1. Field of the Invention

The present invention relates generally to methods for the treatment of cancer. More specifically, the invention relates to methods of treating cancers, such as, acute myeloid leukemia using a combination therapy.

2. Description of the Related Art

Few therapeutic options exist for patients with relapsed or refractory acute myeloid leukemia (AML). A similar dilemma exists for patients with acute myeloid leukemia whose age or comorbid conditions preclude traditional cytarabine- and anthracycline-based regimens. Decitabine and azacitidine are DNA methyltransferase inhibitors that have been adopted as an alternative to high-dose induction chemotherapy for acute myeloid leukemia patients who cannot tolerate or whose disease has failed aggressive induction.

Acute myeloid leukemia is genetically very heterogeneous which has contributed to many failed attempts for targeting any particular mutation (1). Cellular oxidative state is a credible alternative target to selectively eradicate acute myeloid leukemia cells because it is a fundamental property of each cell that is sufficiently different between leukemic and normal cells, yet its aberrancy is shared among different acute myeloid leukemia cells.

Dichloroacetate binds to the active site of pyruvate dehydrogenase kinase and inactivates its kinase activity thus shunting more pyruvate into mitochondria and away from conversion to lactate. Arsenic trioxide is approved for treatment of patients with acute promyelocytic leukemia (APL) whose disease failed to respond to or relapsed following all-trans retinoic acid/anthracycline therapy. In acute promyelocytic leukemia, arsenic trioxide induces both differentiation and apoptosis of leukemic cells (2). High concentrations of arsenic trioxide appear to be a limiting factor for clinical use due to severe treatment-related adverse events.

Thus, the prior art is deficient in methods to treat cancers such as acute myeloid leukemia using a synergistic combination drug treatment. The present invention fulfills this longstanding need and desire in the art.

SUMMARY OF THE INVENTION

The present invention is directed to a formulation comprising dichloroacetate and arsenic trioxide.

The present invention is further directed to a method of treating cancer in a subject, comprising the step of administering to the subject a therapeutically effective amount of dichloroacetate and arsenic trioxide simultaneously or sequentially.

The present invention is further directed to a method of treating cancer in a subject, comprising the steps of administering to the subject a therapeutically effective amount of dichloroacetate for 24-48 hours initially; and subsequently administering to the subject a therapeutically effective amount of dichloroacetate and arsenic trioxide.

Other and further aspects, features, benefits, and advantages of the present invention will be apparent from the following description of the presently preferred embodiments of the invention given for the purpose of disclosure.

BRIEF DESCRIPTION OF DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A shows graphs of percent proliferation of MOLM-14 cells versus vehicle treated with a range of arsenic trioxide (top, $IC_{50}$=0.9450 µM) and dichloroacetate (bottom, $IC_{50}$=15.53 mM) concentrations. FIG. 1B shows graphs of percent proliferation of MV4-11 cells versus vehicle treated with a range of arsenic trioxide (top, $IC_{50}$=0.5753 µM) and dichloroacetate (bottom, $IC_{50}$=21.53 mM) concentrations. FIG. 1C shows graphs of percent proliferation of MonoMac6 cells versus vehicle treated with a range of arsenic trioxide (top, $IC_{50}$=1.218 µM) and dichloroacetate (bottom, $IC_{50}$=25.41 mM) concentrations. FIG. 1D shows graphs of percent proliferation of THP-1 cells versus vehicle treated with a range of arsenic trioxide (top, $IC_{50}$=4.771 µM) and dichloroacetate (bottom, $IC_{50}$=35.08 mM) concentrations. FIG. 1E shows graphs of percent proliferation of AML17 primary acute myeloid leukemia cells from patients versus vehicle exposed to a range of arsenic trioxide (top, $IC_{50}$=3.616 µM) and dichloroacetate (bottom, $IC_{50}$=18.26 mM) concentrations. FIG. 1F shows graphs of percent proliferation of AML18 primary acute myeloid leukemia cells from patients cells versus vehicle exposed to a range of arsenic trioxide (top, $IC_{50}$=1.160 µM) and dichloroacetate (bottom, $IC_{50}$=8.981 mM) concentrations. FIG. 1G shows graphs of percent proliferation of AML20 primary acute myeloid leukemia cells from patients cells versus vehicle exposed to a range of arsenic trioxide (top, $IC_{50}$=0.7028 µM) and dichloroacetate (bottom, $IC_{50}$=9.5513 mM) concentrations. Selected cell proliferation assay results from at least two experiments for each of the two treatments are shown.

FIG. 2A shows the proliferation of MOLM-14 cells. The pretreatment with dichloroacetate at $IC_{30}$ increased the cytotoxicity of arsenic trioxide by 2-fold. FIG. 2B shows a graph of MV4-11 cells where the effect of the sequential combination treatment of dichloroacetate and arsenic trioxide had a potentiation factor of 1.82. FIG. 2C shows a graph of MonoMac-6 cells where the effect of the sequential combination treatment of dichloroacetate and arsenic trioxide had a potentiation factors of 2.16. FIG. 2D shows the sequential administration of low dose dichloroacetate and arsenic trioxide synergistically killed acute myeloid leukemia cells.

FIG. 3A shows a graph of the treatment of MOLM-14 cells with combination of dichloroacetate at their corresponding $IC_{30}$ and arsenic trioxide at their corresponding $IC_{50}$ with priming strategy significantly increased apoptosis compared to arsenic trioxide alone or dichloroacetate alone or their combination without priming. FIG. 3B shows a graph of the treatment of AML-20 cells with combination of dichloroacetate at their corresponding $IC_{30}$ and arsenic trioxide at their corresponding $IC_{50}$ with priming strategy significantly increased apoptosis compared to arsenic trioxide alone or dichloroacetate alone or their combination without priming.

FIG. 4A shows treatment of MOLM-14 cells with combination of dichloroacetate at their corresponding $IC_{30}$ and arsenic trioxide at their corresponding $IC_{50}$ with priming strategy as significantly decreased mitochondrial membrane potential compared to arsenic trioxide alone or dichloroacetate alone or their combination without priming. FIG. 4B shows treatment of AML-20 primary cells with combination of dichloroacetate at their corresponding $IC_{30}$ and arsenic trioxide at their corresponding $IC_{50}$ with priming strategy as significantly decreased mitochondrial membrane potential compared to arsenic trioxide alone or dichloroacetate alone or their combination without priming.

FIG. 5A shows reactive oxygen species levels of MOLM-14 cells with different treatments. With the sequential treatment, 24 hour priming of MOLM-14 cells with $IC_{30}$ of dichloroacetate increased reactive oxygen species production by 167% when compared to PBS control. FIG. 5B shows reactive oxygen species levels after treatment of THP-1 cells with dichloroacetate resulted in increased level of reactive oxygen species production. There was no significant increase in reactive oxygen species production upon treatment with arsenic trioxide alone, concurrent combination of dichloroacetate and arsenic trioxide or the sequential treatment with dichloroacetate ($IC_{30}$) and arsenic trioxide ($IC_{50}$). Up to 4-fold increase in the reactive oxygen species production was detected in leukemia cells after 24 hour of the dichloroacetate treatment when compared to vehicle control. FIG. 5C shows reactive oxygen species levels of AML20 primary AML cells treated with dichloroacetate and/or arsenic trioxide.

FIG. 6A shows reactive oxygen species production by MOLMI-14 cells treated concurrently with increasing doses of arsenic trioxide (up to 10 µM), dichloroacetate (up to 70 mM) and their combination at equal ratio for up to 48 hours. FIG. 6B shows reactive oxygen species production THP-1 cells treated concurrently with increasing doses of arsenic trioxide (up to 10 µM), dichloroacetate (up to 70 mM) and their combination at equal ratio for up to 48 hours. Additional arsenic trioxide had little extra effect on reactive oxygen species generation.

FIG. 7A shows levels of Mcl-1 and GPx in MOLM-14 and THP-1 cells after treatment with arsenic trioxide ($IC_{50}$), dichloroacetate ($IC_{30}$), or the combination of arsenic trioxide and dichloroacetate. FIG. 7B shows levels of myeloid cell leukemia 1 (Mcl-1) and glutahione peroxidase (GPx) by Western Blot in primary acute myeloid leukemia cells from patients treated with the combination of dichloroacetate ($IC_{30}$) and arsenic trioxide ($IC_{50}$), or dichloroacetate or arsenic trioxide alone. In AML20 blasts, there was over 60% reduction in Mcl-1 expression in cells treated with the combination of dichloroacetate and arsenic trioxide was observed. In AML17 and AML20 primary AML cells, GPx were decreased in cells primed with dichloroacetate and treated with dichloroacetate and arsenic trioxide when compared to cells treated without priming.

DETAILED DESCRIPTION OF THE INVENTION

Figure 1A:
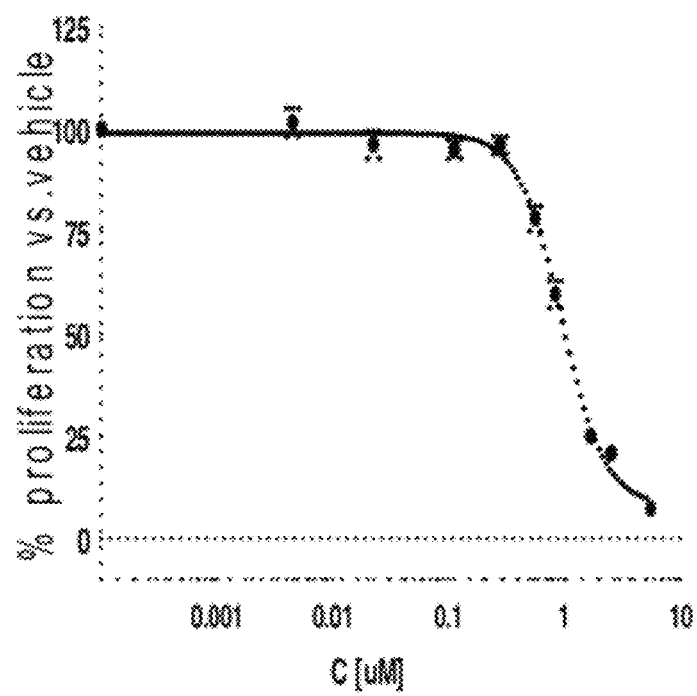
FIGS. 1A-1G show acute myeloid leukemia cell lines and primary cells with or without a FLT3-ITD (Fms-like tyrosine kinase 3-internal tandem duplication) mutation are sensitive to arsenic trioxide and dichloroacetate treatment.
Figure 1A:
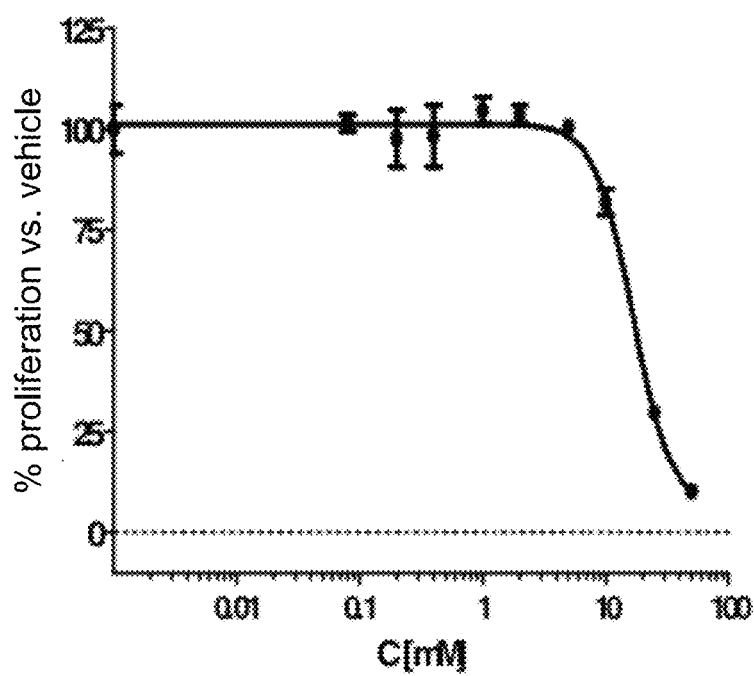

In one embodiment of the present invention, there is provided a formulation comprising dichloroacetate and arsenic trioxide. A person having ordinary skill in this art would readily be able to determine useful concentrations of dichloroacetate and arsenic trioxide that would result in a formulation useful to treat a cancerous condition. In one preferred aspect, the dichloroacetate is contained in the formulation in an amount of about 1 mM to about 50 mM. In one preferred aspect, the arsenic trioxide is contained in the formulation in an amount of about 0.1 µM to about 10 µM. In one aspect of the invention, the formulation is a pharmaceutical composition. Representative examples of pharmaceutical forms include but are not limited to a suspension, spray, solution, gel, paste, ointment, cream, nanoparticle, liposome, microcapsule, delivery device or powder. Preferably, the pharmaceutical composition contains one or more physiologically acceptable carriers and/or excipients. The pharmaceutical composition may be administered via oral, subcutaneous, intravenous, intraperitoneal, ocular, intradermal, intranasal, or intramuscular routes. The pharmaceutical composition may be administered one or more times to achieve a therapeutic or an immunogenic effect. It is well within the skill of an artisan to determine dosage or whether a suitable dosage comprises a single administered dose or multiple administered doses. An appropriate dosage depends on the subject's health, the progression or remission of the disease, the route of administration and the formulation used.

In another embodiment of the present invention, there is provided a method of treating cancer in a subject, comprising the step of administering to the subject a therapeutically effective amount of dichloroacetate and arsenic trioxide. Representative examples of a cancer which may be treated using this method of the present invention include, but are not limited to, leukemia, breast cancer, pancreatic cancer, colorectal cancer, lung cancer, skin cancer or prostate cancer. In one preferred embodiment, the leukemia is acute myeloid leukemia. For example, the acute myeloid leukemia may be relapsed or refractory acute myeloid leukemia. In another preferred embodiment, the subject has a FLT3-ITD (Fms-like tyrosine kinase 3-internal tandem duplication) mutation. In this method of the present invention, the dichloroacetate and arsenic trioxide may be administered simultaneously or sequentially in a synergistic combination. For example, the synergistic combination has a more than additive effect. As discussed above, a person having ordinary skill in this art would readily be able to determine the appropriate dosage for dichloroacetate and arsenic trioxide useful to treat the indicated cancer. Generally, the dichloroacetate is administered in a concentration of about 5 mg/kg to about 50 mg/kg of the subject's body weight daily. Generally, the arsenic trioxide is administered in a concentration of about 0.1 mg/kg to about 0.2 mg/kg of the subject's body weight daily. Preferably, the dichloroacetate and/or arsenic trioxide are administered by an route of adminstration useful to treat the specific cancer. Representative routes of administration include, but are not limited to, oral administration and intravenous administration. In a preferred embodiment of the present invention, the patient is first treated with dichloroacetate and then treated with a combination of arsenic trioxide and dichloroacetate. Preferably, the first treatment of dichloroacetate is administered for a period of time of 24-48 hours. In one preferred embodiment, the first treatment of dichloroacetate is administered at a sub-therapeutic dose. For example, a representative sub-therapeutic dose of dichloroacetate would be at the $IC_{30}$.

In another embodiment of the present invention, there is provided a method of treating cancer in a subject, comprising the steps of administering to the subject a therapeutically effective amount of dichloroacetate for 24-48 hours; and administering to the subject a therapeutically effective amount of dichloroacetate and arsenic trioxide. Representative cancers which may be treated using this method of the present invention include but are not limited to cancer is leukemia, breast cancer, pancreatic cancer, colorectal cancer, lung cancer, skin cancer or prostate cancer. In a preferred aspect, the leukemia is acute myeloid leukemia. Preferably, the dichloroacetate is administered in a concentration of about 5 mg/kg to about 50 mg/kg of the subject's body weight daily and the arsenic trioxide is administered in a concentration of about 0.1 mg/kg to about 0.2 mg/kg of the subject's body weight daily.

As is well known in the art, the methods of the present invention may be administered to either human or non-human subjects.

As is well known in the art, the methods of the present invention may be administered alone or in combination with one or more other commonly used cancer chemotherapeutic agents to a subject to treat a particular condition.

As related to the present invention, the term "priming" is defined as treatment with a low ($IC_{30}$) dose of dichloroacetate for 24-48 hours before treatment with the arsenic trioxide and dichloroacetate. As related to the present invention, the term "$IC_{50}$" is defined as the inhibitory concentration that inhibits proliferation of 50% cells. As related to the present invention, the term "$IC_{30}$" is defined as the inhibitory concentration that inhibits proliferation of 30% cells. As related to the the present invention, the phrase "potentiation factor" is defined as the reverse ratio of $IC_{50}$ when cells were treated with dichloroacetate and arsenic trioxide compared to vehicle and arsenic trioxide.

The following examples are given for the purpose of illustrating various embodiments of the invention and are not meant to limit the present invention in any fashion.

EXAMPLE 1

$IC_{50}$ Determination for Dichloroacetate and Arsenic Trioxide

MOLM-14 and MV4-11 cells, which carry FLT3-ITD mutation, MonoMac6 cells, which carry a FLT3-V592A activating single point mutation and THP-1 cells, which are FLT3 wild type cells, and primary leukemia blasts isolated from acute myeloid leukemia patients with or without FLT3-ITD mutation were seeded in 96 well plates. Dichloroacetate (DCA) (0.08-100 mM) or arsenic trioxide (ATO) (0.0045-5.055 µM) were added at different concentrations and control wells were treated with an equivalent volume of the vehicle for each drug. Cells were cultured in the presence of the drugs for 72 hours or 48 hours for the primary cells and terminated by the addition of WST-1 reagent.

Figure 1B:
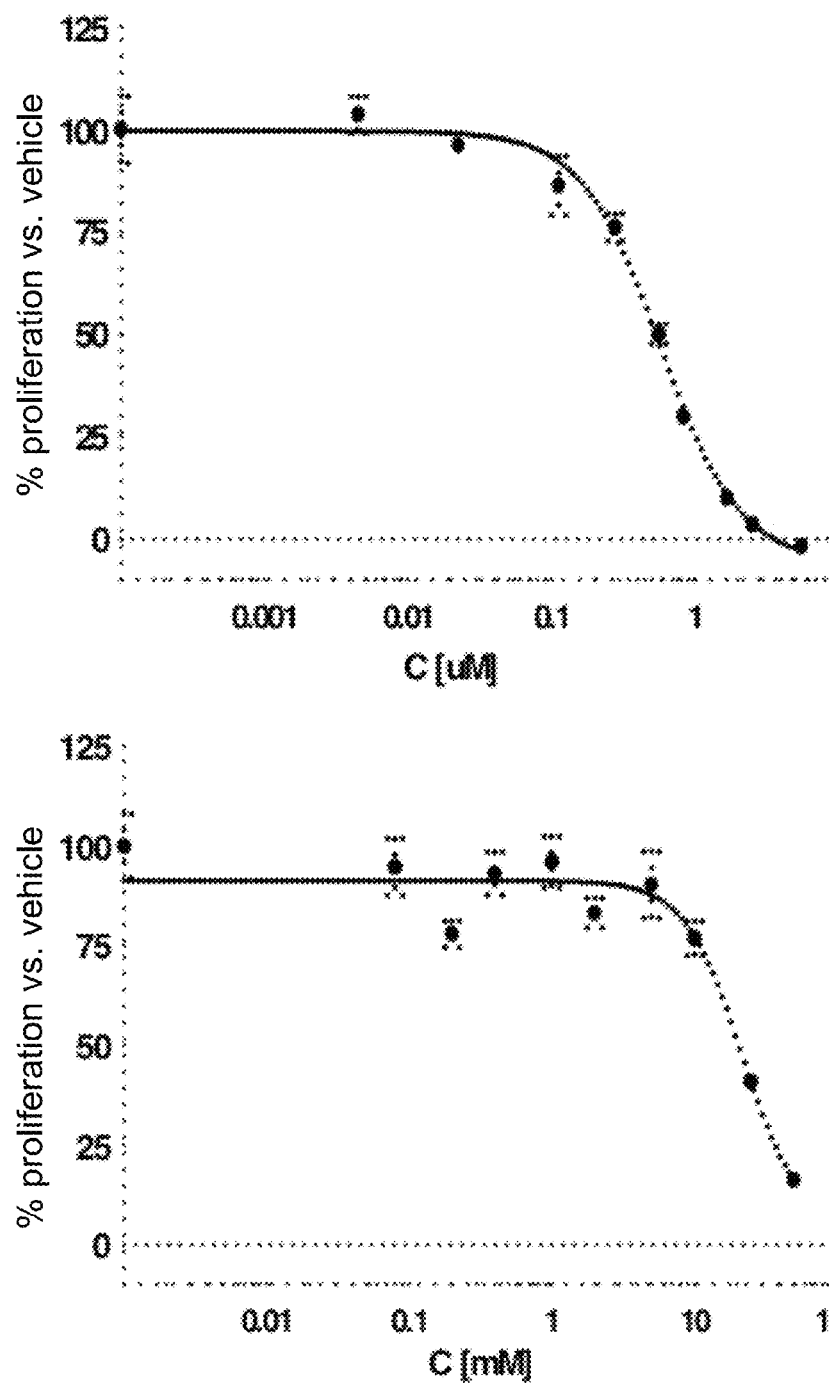
Figure 1C:
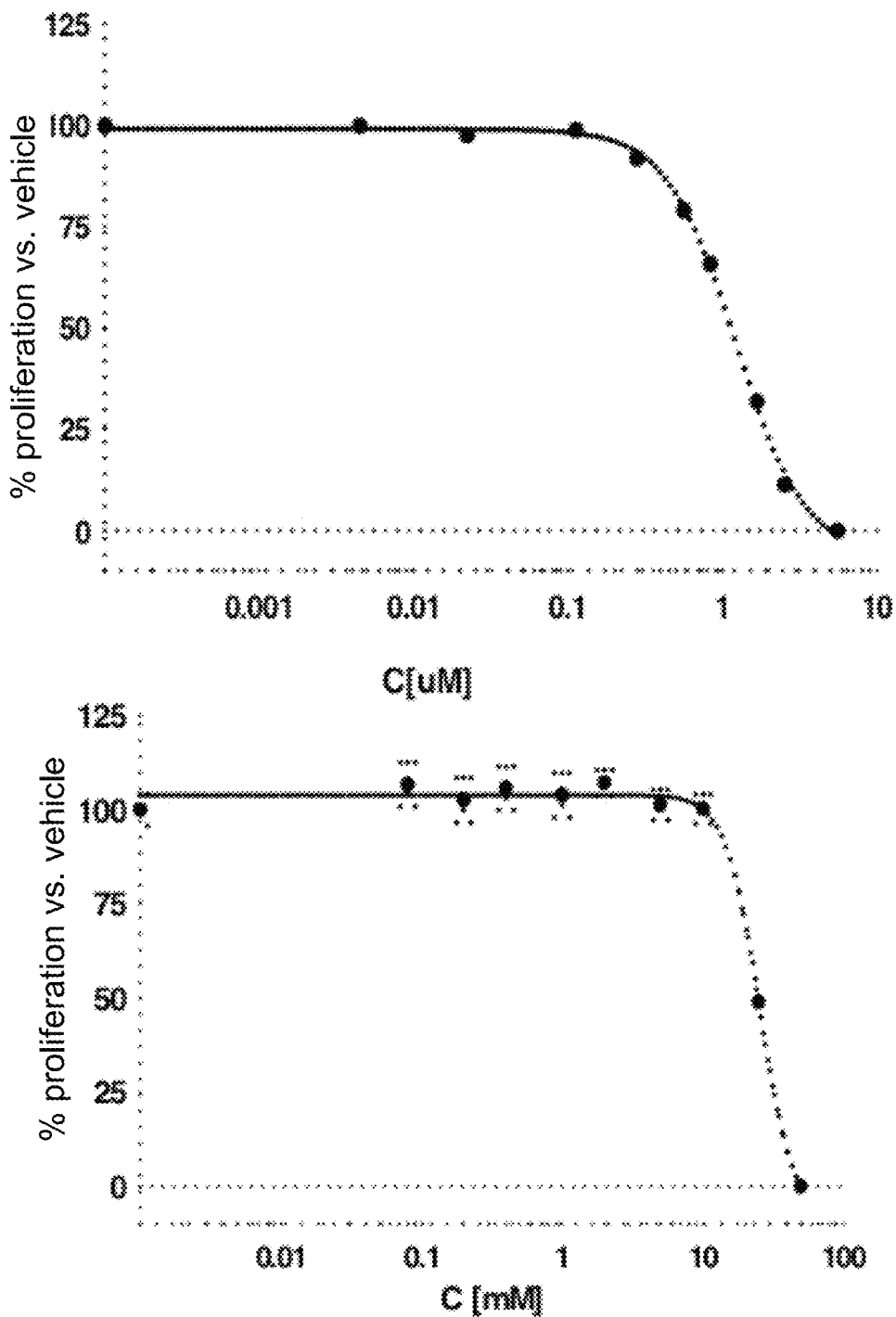
Figure 1D:
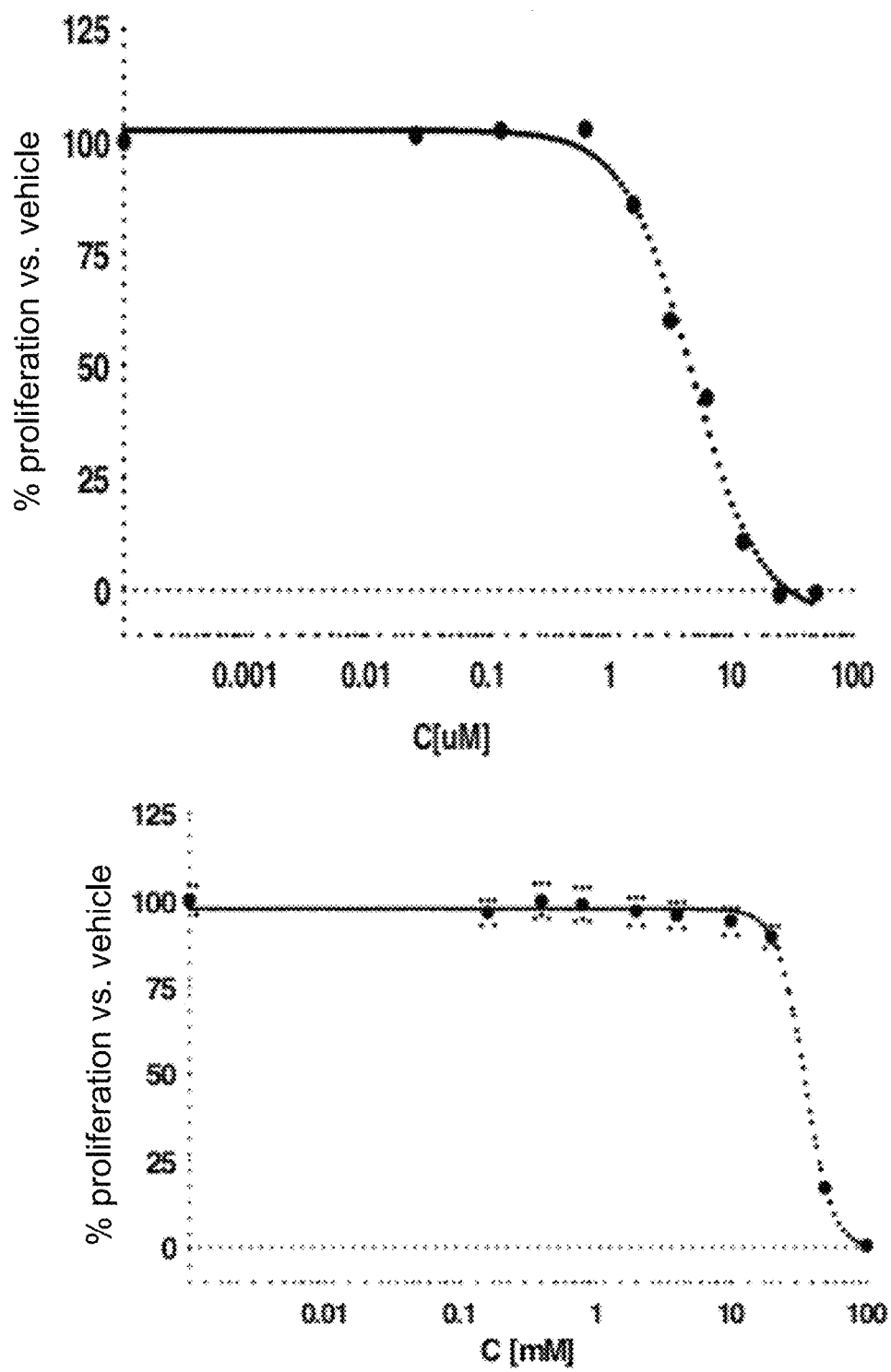
Figure 1E:
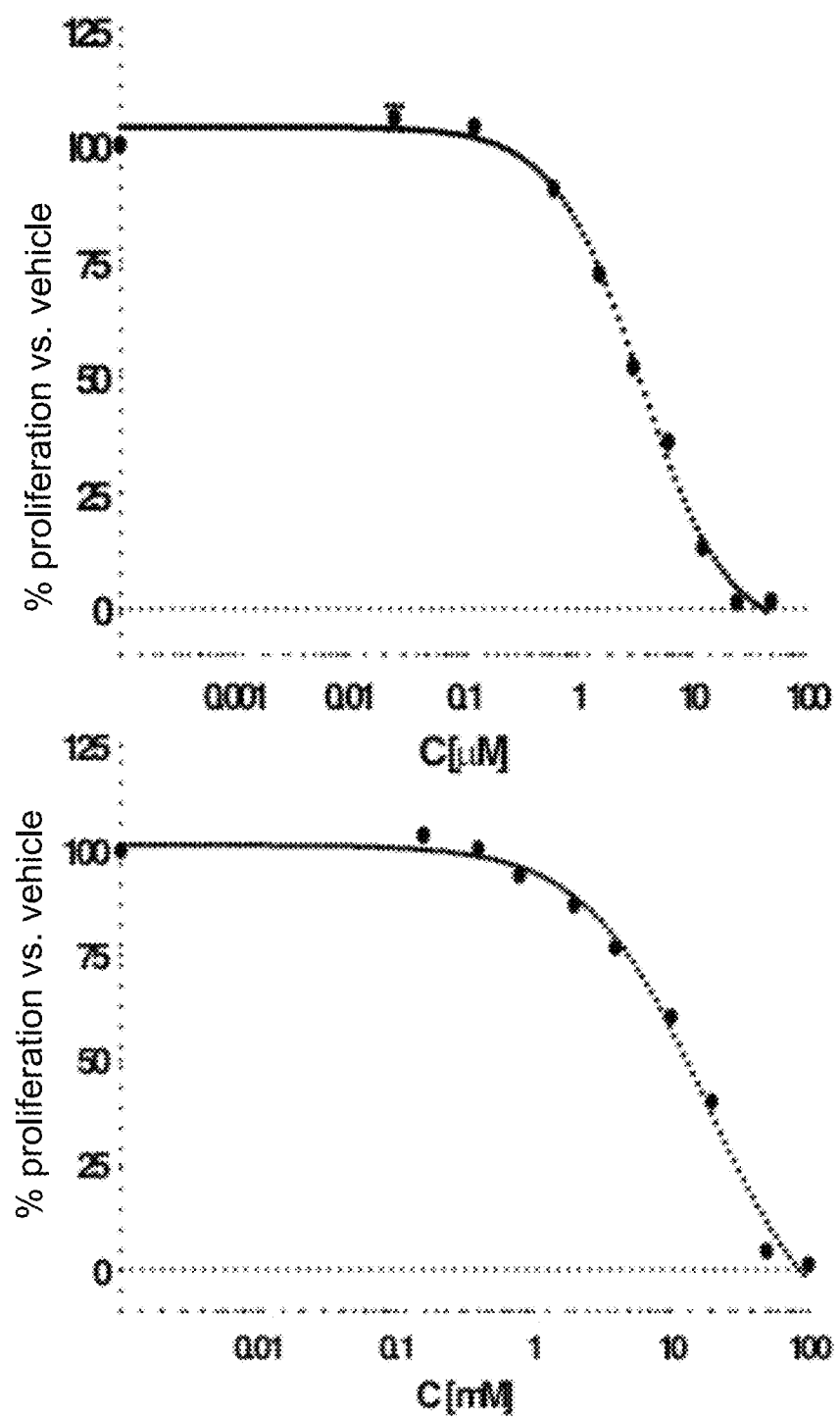
Figure 1F:
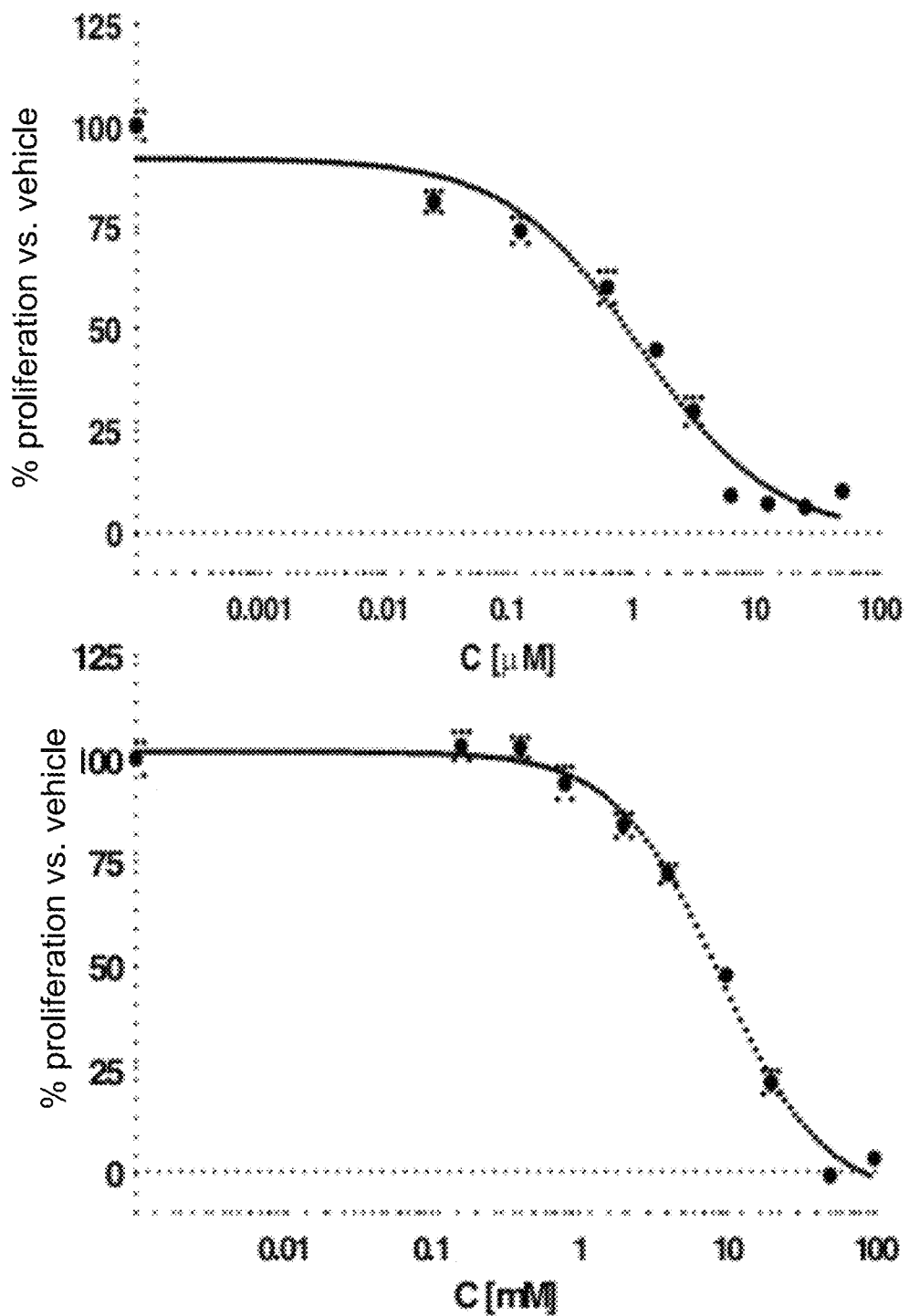
Figure 1G:
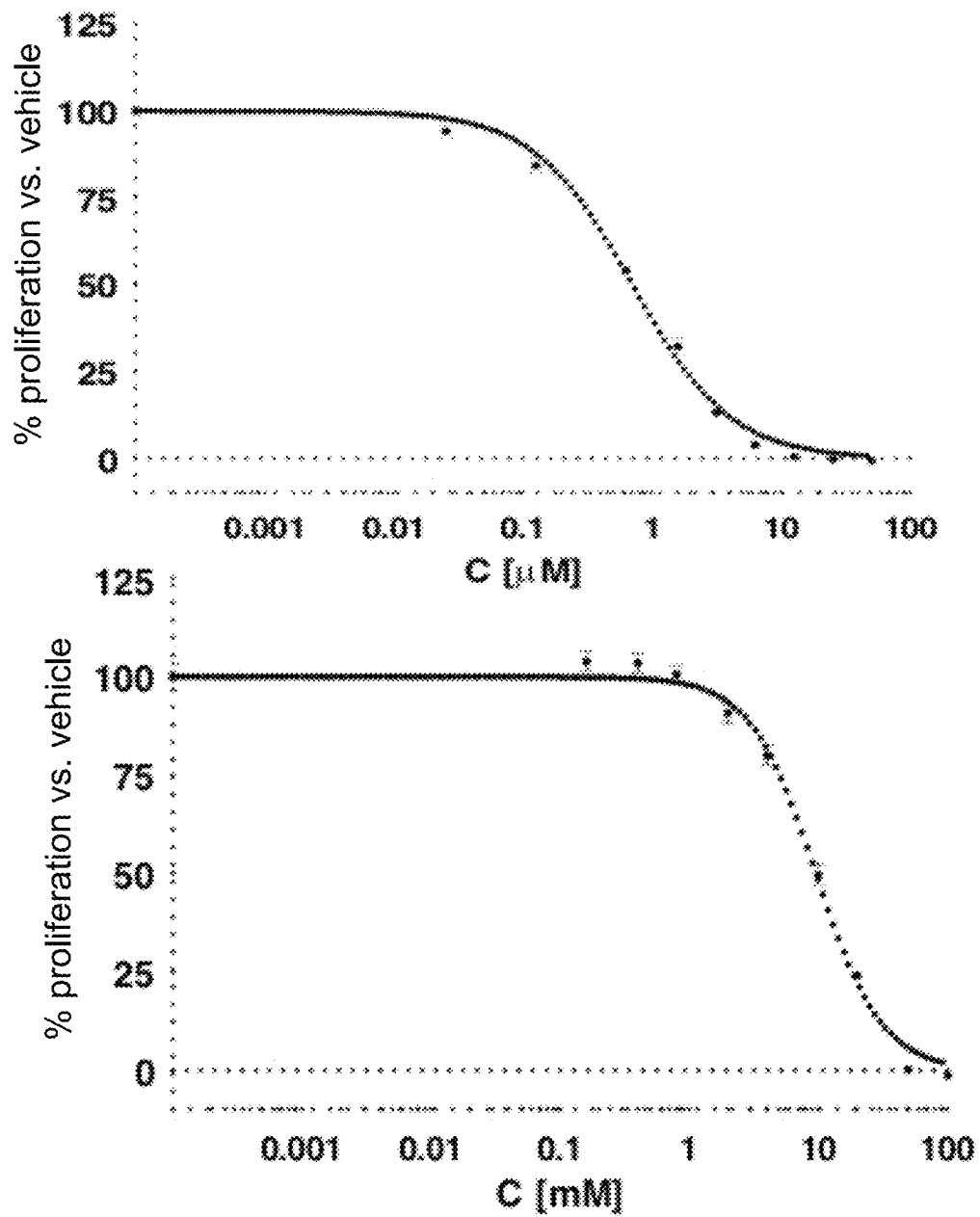

Cell lines carrying the FLT3-ITD mutation as well as FLT3-WT were sensitive to arsenic trioxide and dichloroacetate (FIG. 1A). $IC_{50}$ values for arsenic trioxide and dichloroacetate were obtained: 0.88±0.04 µM and 15.9±1.2 mM for MOLM-14, 0.53±0.03 µM and 19.1±2.3 mM for MV4-11, 1.08±0.1 µM and 25.1±2.0 mM for MonoMac-6, and 4.68±0.13 µM and 35.5±0.3 mM for THP-1, respectively (FIG. 1A, Table 1). For primary leukemia cells (AML17, AML18, and AML20) the $IC_{50}$ values ranged from 0.70 to 4.35 µM for arsenic trioxide and from 9.6 to 19.4 mM for dichloroacetate, respectively (FIG. 1B, Table 1). MOLM-14 and MV4-11 cells appeared to be more sensitive to arsenic trioxide and dichloroacetate, compared to THP-1 cells.

EXAMPLE 2

Drug Combination Studies of Cytotoxicity of Arsenic Trioxide and Dichlororacetate on Leukemic Cells MOLM-14, MV4-11, MonoMac6 and AML 18 cells were treated with arsenic trioxide alone at $IC_{50}$ or sequentially first with dichloroacetate at the $IC_{30}$ concentration of 11 nM for 48 hours and then arsenic trioxide in the presence of freshly added dichloroacetate daily. The cytotoxic effect of arsenic trioxide was potentiated 1.3-2.1 times when sequentially combined (primed) with low dose dichloroacetate (FIGS. 2A-2D). Sequential administration of low dose dichloroacetate and arsenic trioxide synergistically killed acute myeloid leukemia cells. Table 1 shows the cytotoxic effects of dichloroacetate, arsenic trioxide or their combination on acute myeloid leukemia cell lines and primary acute myeloid leukemia cells from patients. Leukemia cells showed sensitivity to dichloroacetate, arsenic trioxide and sequential (priming) combination of both drugs. $IC_{50}$ values were calculated as average±standard deviation from at least two independent experiments.

TABLE 1

Cytoxicity of dichloroacetate and arsenic trioxide

| Cell | FLT3 Status | $IC_{50}$ ATO (µM) | $IC_{50}$ DCA (mM) | $IC_{50}$ of ATO primed with DCA ($IC_{30}$) vs $IC_{50}$ of ATO alone (PF) | Decreased Cell Viability | CI |
|---|---|---|---|---|---|---|
| MOLM-14 | ITD | 0.88 ± 0.04 | 15.9 ± 1.2 | 0.78 vs 1.60 (2.0) | 44% | 0.80 |
| MV4-11 | ITD | 0.53 ± 0.03 | 19.1 ± 2.3 | 1.13 vs 2.06 (1.82) | 93% | — |
| MonoMac6 | V592A | 1.08 ± 0.1 | 25.1 ± 2.0 | 0.88 vs 1.9 (2.16) | 75% | 0.81 |

TABLE 1-continued

Cytoxicity of dichloroacetate and arsenic trioxide

| Cell | FLT3 Status | IC$_{50}$ | | IC$_{50}$ of ATO primed with DCA (IC$_{30}$) vs IC$_{50}$ of ATO alone (PF) | Decreased Cell Viability | CI |
|---|---|---|---|---|---|---|
| | | ATO (µM) | DCA (mM) | | | |
| | mutation | | | | | |
| THP-1 | WT | 4.68 ± 0.13 | 35.5 ± 0.3 | 5.46 vs 4.55 (0.87) | 20% | 1.1 |
| AML17 | WT | 4.35 ± 1.3 | 19.4 ± 1.6 | 1.53 vs 2.75 (1.80) | — | 0.71 |
| AML18 | ITD | 1.22 ± 0.08 | 9.9 ± 1.3 | 1.41 vs 1.87 (1.33) | — | 0.62 |
| AML20 | WT | 0.7 | 9.6 | — | — | — |

Figure 2A:
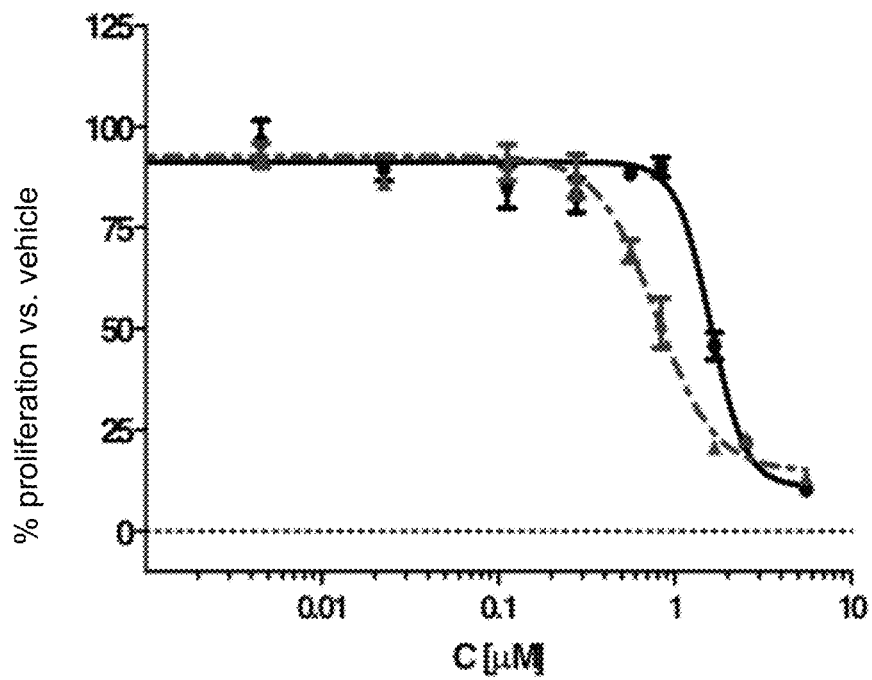
FIGS. 2A-2D show graphs of percent proliferation of MOLM-14, MV4-11, MonoMac-6 and AML18 primary cells treated with arsenic trioxide alone at $IC_{50}$ or sequentially first with dichloroacetate at the $IC_{30}$ concentration for 48 hours and then arsenic trioxide in the presence of freshly added dichloroacetate daily.
Figure 2B:
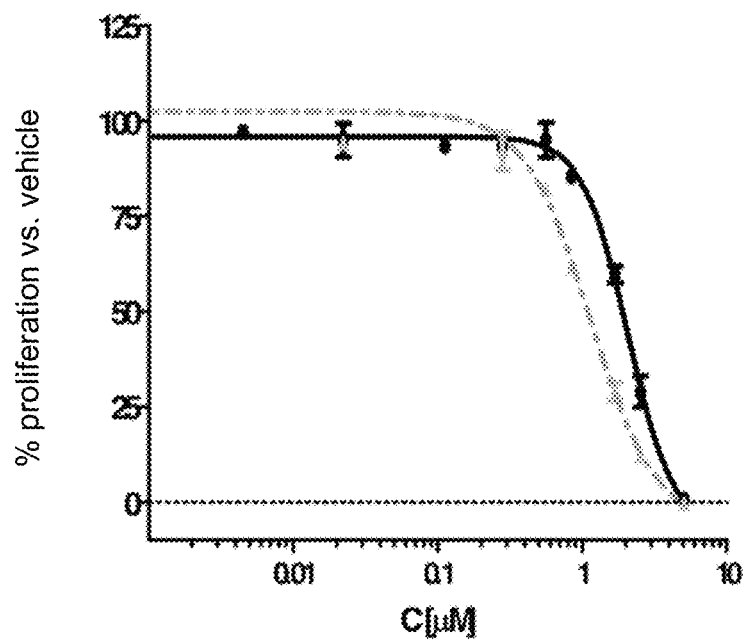
Figure 2C:
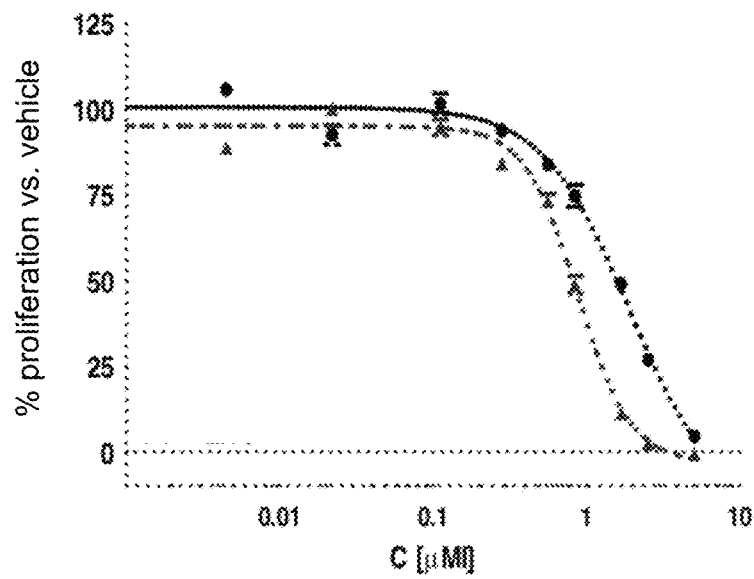
Figure 2D:
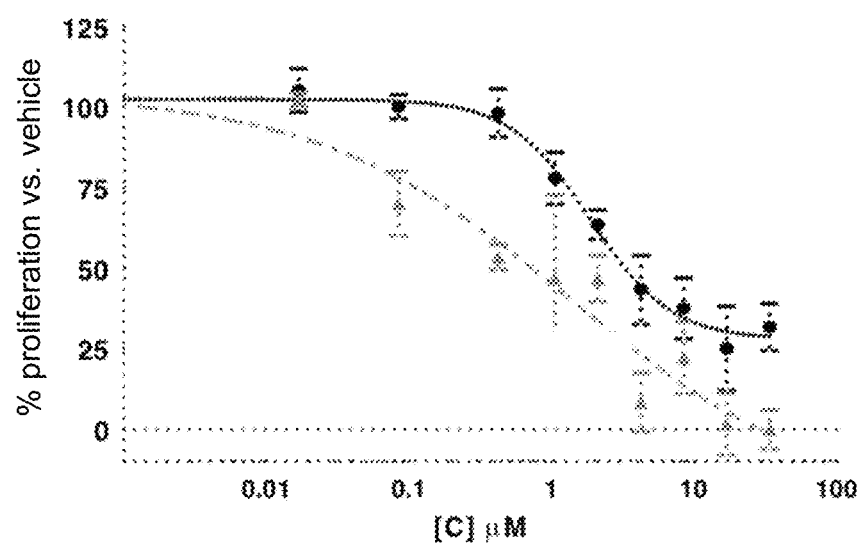

In MOLM-14 cells, the pretreatment with dichloroacetate at IC$_{30}$ increased the cytotoxicity of arsenic trioxide by 2-fold (FIG. 2A). In MV4-11 and MonoMac-6 cells the effect of the sequential combination treatment was similar with potentiation factors (PF) of 1.82 and 2.16, respectively (FIG. 2B-2C). Priming primary acute myeloid leukemia cells with dichloroacetate increased the cytotoxicity of arsenic trioxide by 1.3 to 1.8-fold (Table 1). Trypan blue exclusion confirmed decreased cell viability by 20-93% in both FLT3-ITD and FLT3-WT cell lines when cells were treated with the sequential combination regimen (Table 1).

To determine if the two agents were acting synergistically when sequentially combined against the leukemia cells, Isobolic analysis was performed based on WST-1 cell proliferation data and combination indices (CIs) were calculated. Combination of dichloroacetate and arsenic trioxide demonstrated a synergistic anti-leukemic effect (CI<0.9) on MOLM-14, MonoMac6, AML17, and AML18 with CIs of 0.80, 0.81, 0.71 and 0.62, respectively (Table 1). The combination showed an additive effect on THP-1 cells (CI=1.1).

EXAMPLE 3

Induction of Apoptosis in Leukemia Cells

Figure 3A:
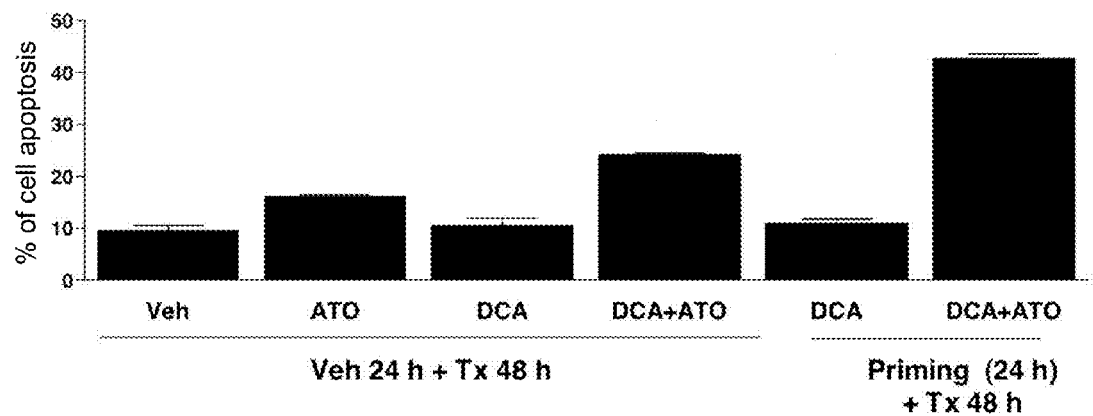
FIGS. 3A-3B show a comparison of apoptosis in MOLM-14 and acute myeloid leukemia cells with different treatment strategies with dichloroacetate and/or arsenic trioxide.
Figure 3B:
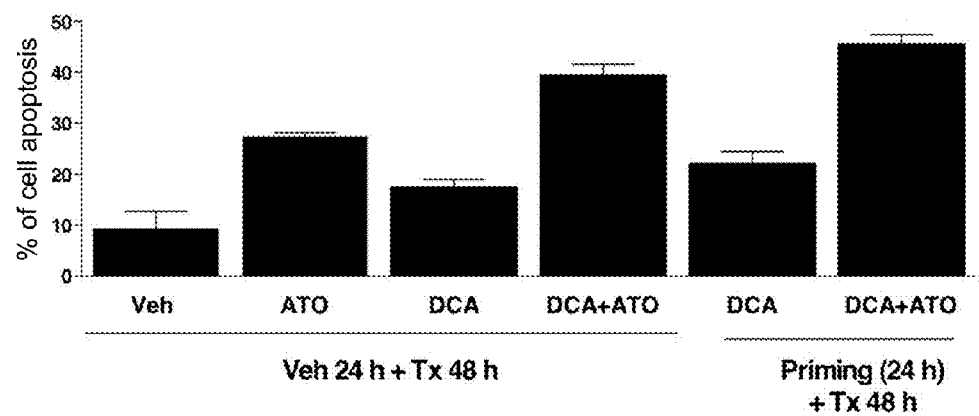

Leukemia cells were first primed with dichloroacetate or vehicle control (PBS) for 24 hours, and then treated with fresh dichloroacetate at IC$_{30}$, arsenic trioxide at IC$_{50}$ or their combination for 24 hours in primary cells or 48 hours in cell lines (FIG. 3A-3B). A flow cytometric assay was used to measure apoptosis. Treatment of MOLM-14 cells with combination of dichloroacetate and arsenic trioxide increased the cells apoptosis by 50% when compared to treatment with arsenic trioxide alone (FIG. 3A). However, priming of cells with dichloroacetate followed by treatment with dichloroacetate and arsenic trioxide, significantly increased the apoptosis by 165% vs. arsenic trioxide alone. In addition, cells primed with dichloroacetate and treated with dichloroacetate and arsenic trioxide showed increase of apoptosis by 296% when compared to cells treated only with dichloroacetate. The dichloroacetate priming increased cell apoptosis by 77.3% when compared to cells treated with dichloroacetate and arsenic trioxide without priming. In the primary cells AML20, combination of dichloroacetate arsenic trioxide increased cell apoptosis by 43.8% vs. arsenic trioxide alone (FIG. 3B). With the dichloroacetate priming, apoptosis rate was increased 66.4% when compared to cells treated with arsenic trioxide alone. Cells primed with dichloroacetate and treated with dichloroacetate and arsenic trioxide had an increased rate of apoptosis by 107% when compared to dichloroacetate alone. The apoptotic effects of dichloroacetate and arsenic trioxide against AML20 were not statistically different in the presence or absence of dichloroacetate priming (FIG. 3B).

EXAMPLE 4

Figure 4A:
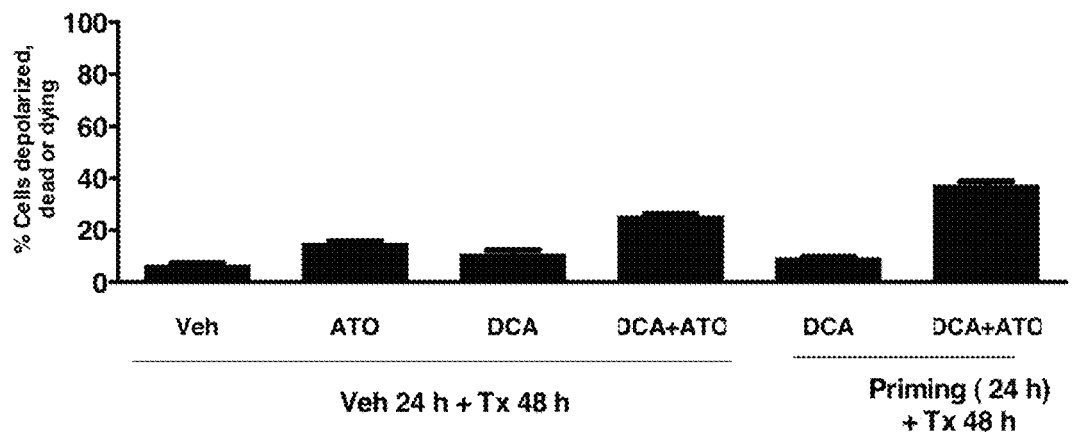
FIGS. 4A-4B show a comparison of induction of depolarization of the mitochondrial transmembrane potential in MOLM-14 and acute myeloid leukemia cells with different treatment strategies with arsenic trioxide and/or dichloroacetate.

Induction of Membrane Depolarization with Dichloroacetate and/or Arsenic Trioxide in Leukemic Cells Flow cytometry with MitoPotential Red stain was used to test whether the treatment with dichloroacetate, arsenic trioxide or sequential combination could significantly induce depolarization of the transmembrane potential resulting in the release of apoptogenic factors. Forty-eight hours concurrent treatment of MOLM-14 cells with dichloroacetate at IC$_{30}$ and arsenic trioxide at IC$_{50}$ decreased mitochondrial membrane potential by 79% compared to arsenic trioxide alone (FIG. 4A).

Figure 4B:
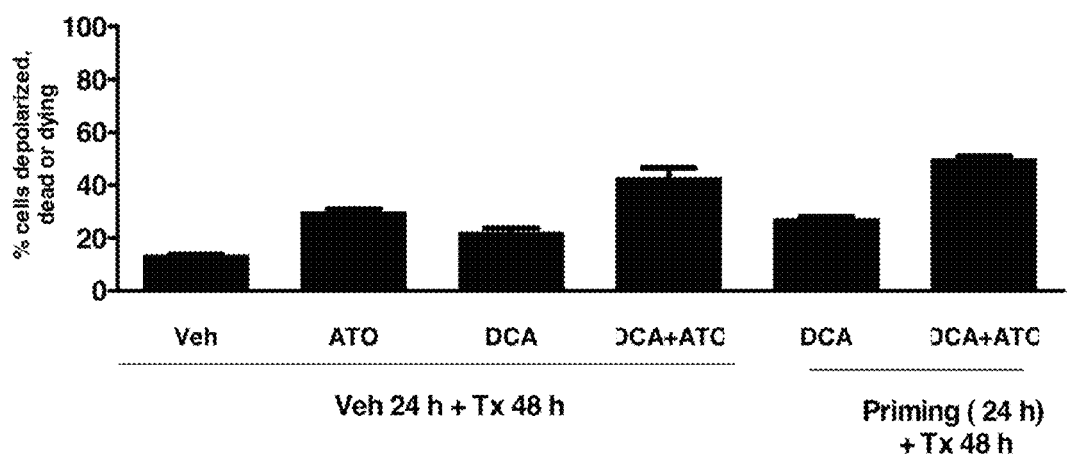

In contrast, priming of MOLM-14 cells followed by treatment with arsenic trioxide at similar doses for 48 hours resulted in a 149% decrease in mitochondrial transmembrane potential compared to arsenic trioxide alone. Transmembrane potential was decreased by 46% when priming occurred compared to concurrent presence of the two agents. In AML20, priming the cells with dichloroacetate at IC$_{30}$ for 24 hours followed by treatment with arsenic trioxide at IC$_{50}$ for 48 hours resulted in a 68% and 84% decrease in mitochondrial transmembrane potential compared to arsenic trioxide alone and dichloroacetate alone, respectively (FIG. 4B). Compared to the concurrent use, sequential treatment with dichloroacetate (priming) and arsenic trioxide increased the loss of transmembrane potential by 16%, but the difference was not statistically significant.

EXAMPLE 5

Production of Reactive Oxygen Species (ROS) in Leukemia Cells

Figure 5A:
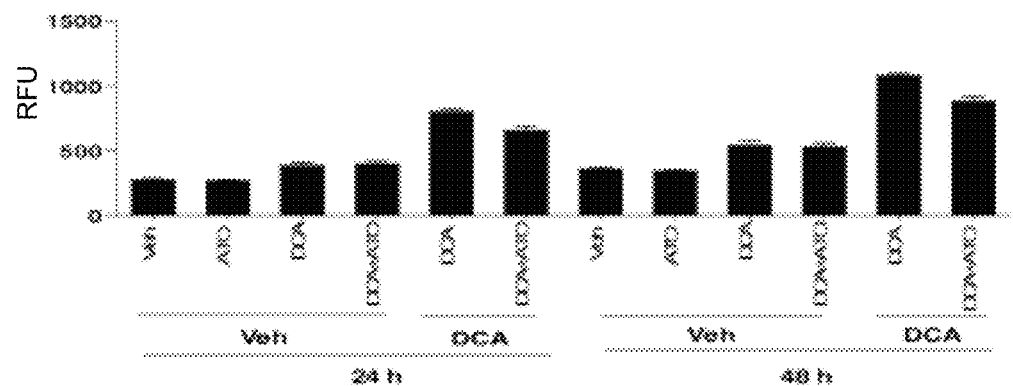
FIGS. 5A-5C shows dichloroacetate augments reactive oxygen species (ROS) production in acute myeloid leukemia cell lines with hydrogen peroxide (H2O2) as a positive control in all treatments.
Figure 5B:
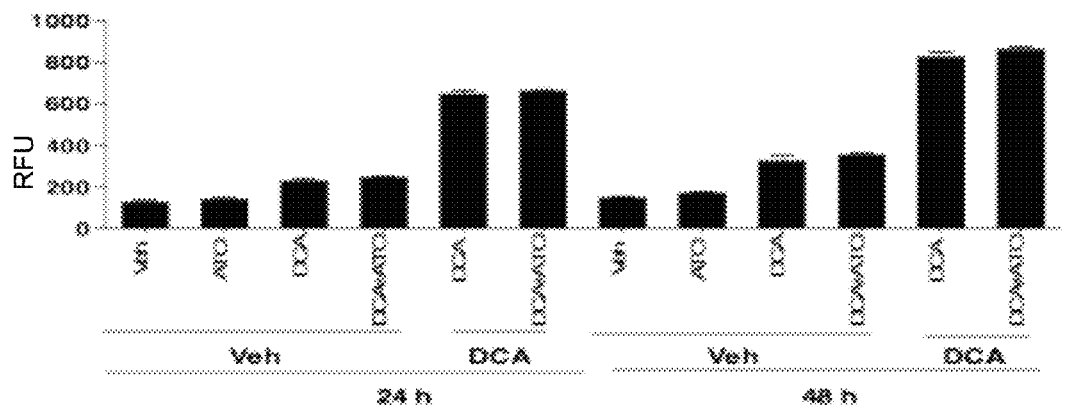
Figure 5C:
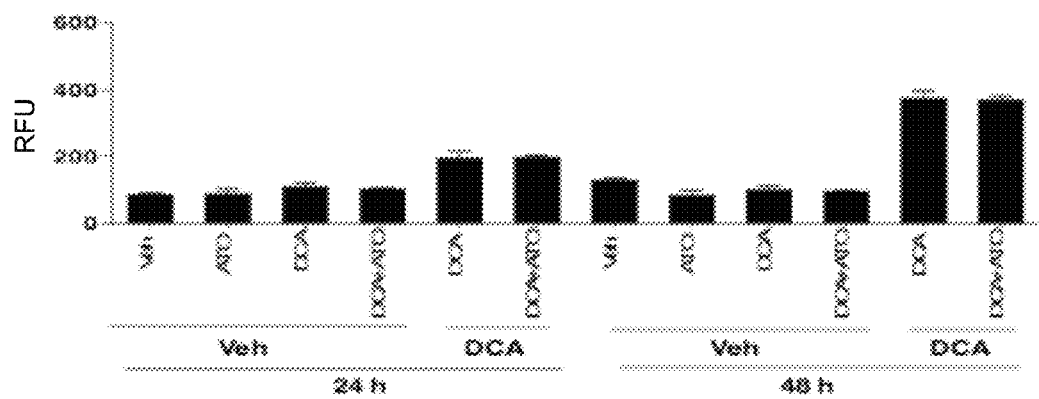
Figure 6A:
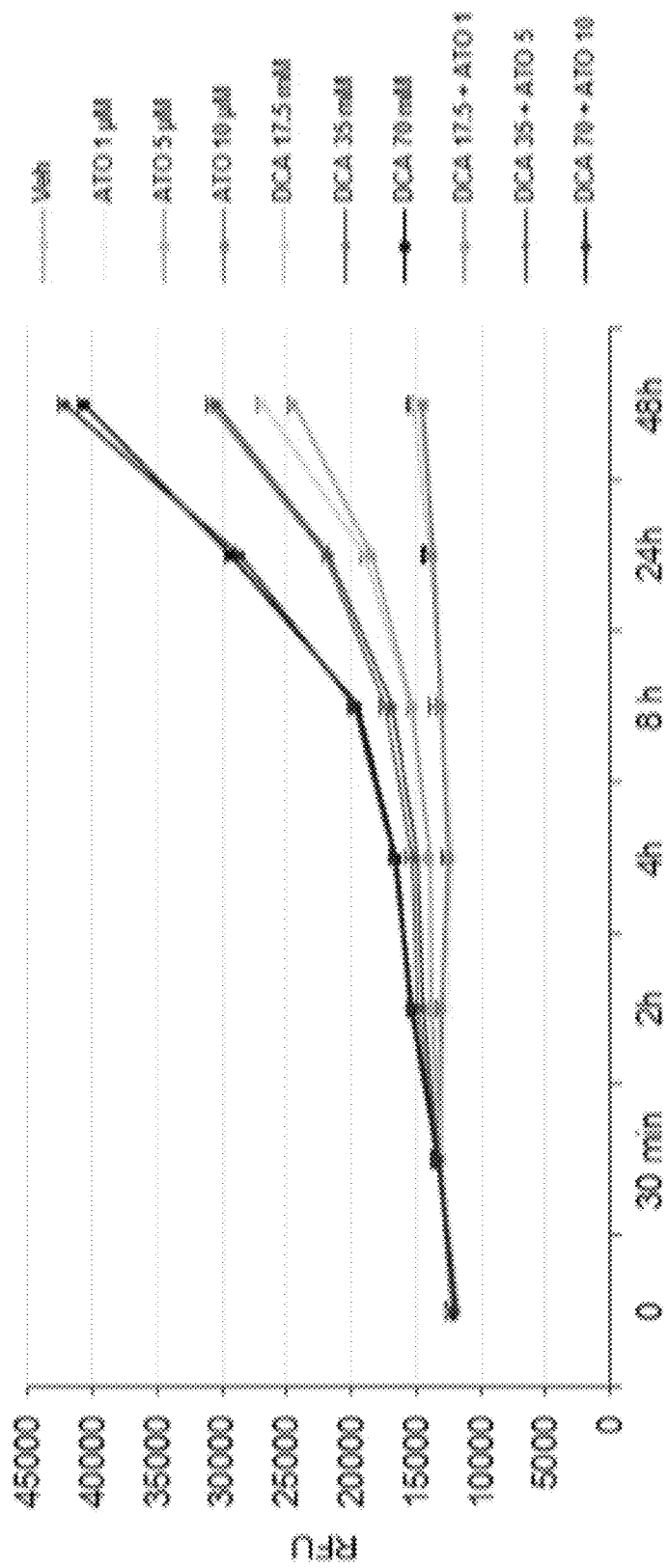
FIGS. 6A-6B show reactive oxygen species production in acute myeloid leukemia cell lines after treatment with dichloroacetate.
Figure 6B:
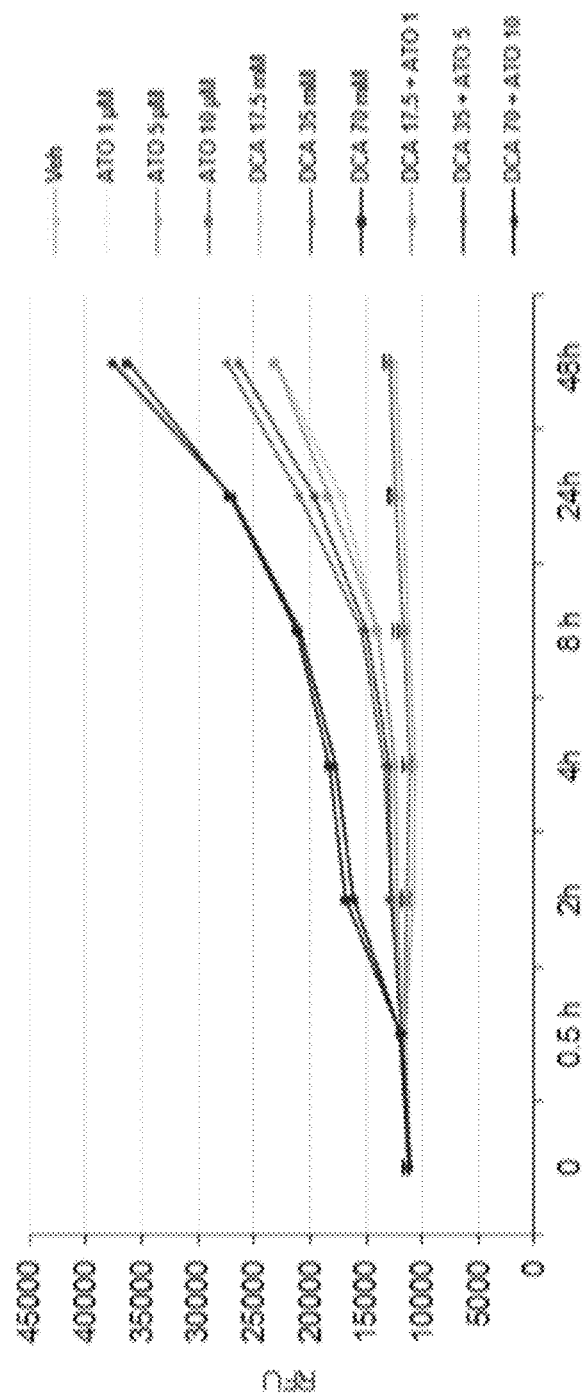

Leukemic cells were stained with the C2',7'-dichlorodihidro-fluoroscein diacetate probe and treated with different concentrations of dichloroacetate and arsenic trioxide for various length of time. In both MOLM-14 and THP-1 cells, a significant increase in reactive oxygen species production was observed after 24 hour exposure to dichloroacetate (FIGS. 5A-5B). With the sequential treatment, 24 hour priming of MOLM-14 cells with IC$_{30}$ of dichloroacetate increased reactive oxygen species production by 167% when compared to PBS control (FIG. 5A). Similar results were observed in THP-1 cells and primary AML20 cells (FIGS. 5B-5C). Cellular reactive oxygen species was elevated by almost 2-fold higher levels in MOLM-14 cells with FLT3-ITD mutation compared with FLT3-WT THP-1 cells. There was no additional increase in intracellular reactive oxygen species after addition of arsenic trioxide to dichloroacetate, as tested by this assay. MOLM-14 and THP-1 cells were treated with increased concentrations of arsenic trioxide (up to 10 µM) and dichloroacetate (up to 70 mM) and the amount of cellular reactive oxygen species was measured (FIGS. 6A-6B). There was no increase in reactive oxygen species production upon treatment of cells with arsenic trioxide alone up to 5 µM concentration. High concentrations of arsenic trioxide (10 µM) induced ROS production. There was also no extra increase in reactive oxygen species generation when arsenic trioxide was used in combination with dichloroacetate compared to dichloroacetate alone, indicating that in acute myeloid leukemia cell lines that reactive oxygen species production mainly was driven by dichloroacetate.

EXAMPLE 6

Decrease Expression of Mcl-1 and Glutathione Peroxidase in Primary AML Cells

Figure 7A:
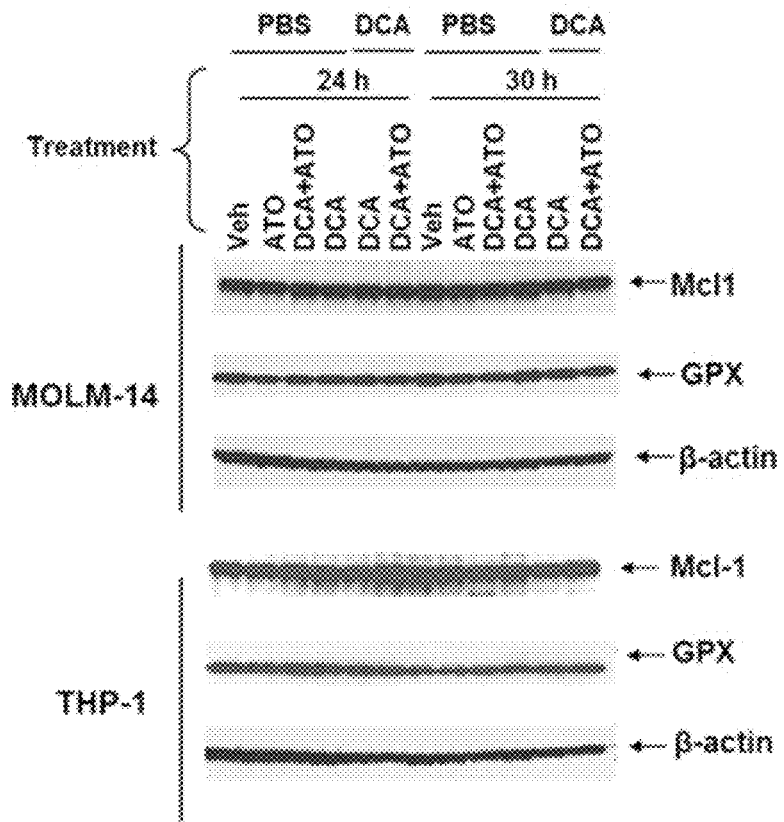
FIGS. 7A-7B show Western Blots of leukemic cells after treatment with the combination of low dose dichloroacetate and arsenic trioxide at $IC_{50}$.
Figure 7B:
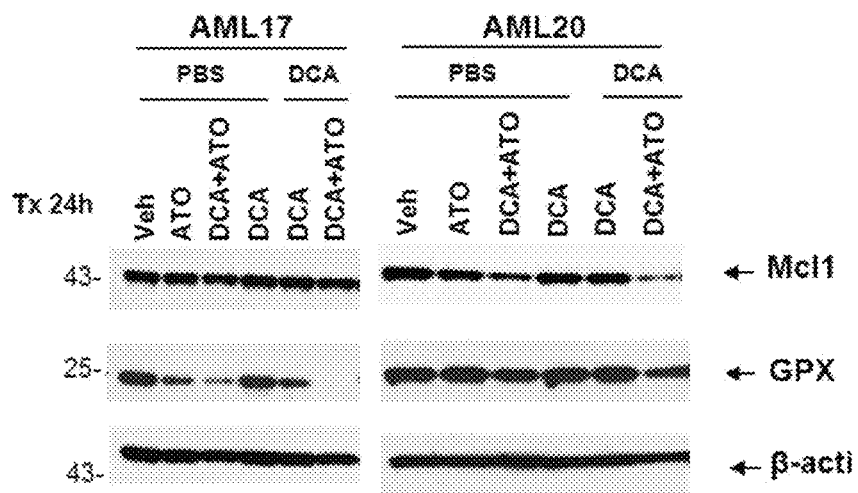

Mcl-1 levels were measured in two acute myeloid leukemia cell lines (MOLM-14 and THP-1) and two acute myeloid leukemia cells derived from patients (AML17 and AML20) by Western Blot after 24-30 hour treatment with arsenic trioxide alone or after priming with dichloroacetate (FIGS. 7A-7B). No significant changes in Mcl-1 expression were observed in cryopreserved MOLM-14, THP-1 and AML17 cells (FIG. 7A). However, in freshly used AML20 blasts, a significant reduction in Mcl-1 expression in cells treated with arsenic trioxide, particularly when primed with dichloroacetate, was observed (FIG. 7B).

Glutathione peroxidase (GPx) levels were measured by Western Blot. Similar to Mcl-1, GPx levels did not change in acute myeloid leukemia cell lines MOLM-14 and THP-1 (FIG. 7A). However, in AML17, GPx was significantly decreased with the combination of dichloroacetate and arsenic trioxide (FIG. 7B). In AML20, GPx level was decreased more after treatment with combination of dichloroacetate and arsenic trioxide compared to either drug alone.

EXAMPLE 7

Treatment of Refractory Acute Myeloid Leukemia

A 23 year old patient with refractory extramedullary acute myeloid leukemia who received a total of 8 prior lines of chemotherapy was treated with the combination of dichloroacetate and arsenic trioxide. The drugs were administered after discussing the case with the patient and his parents, obtaining written informed consent and Institutional Review Board (IRB) approval as well as permission from the FDA.

The patient was treated with dichloroacetate 12.5 mg/kg orally twice a day. This dose was chosen based on previous clinical use of dichloroacetate in patients with brain tumors. Arsenic trioxide (0.15 mg/Kg intravenously daily) was started after the 4th dose of dichloroacetate (48 hour after starting dichloroacetate). The patient received dichloroacetate for 11 days and arsenic trioxide for 9 days. The patient was closely monitored for tumor lysis syndrome; no evidence of lysis requiring intervention was observed. EKG was regularly monitored per institutional guidelines and remained normal. The patient tolerated the combination of dichloroacetate and arsenic trioxide well without experiencing serious treatment related adverse events. He had mild peripheral neuropathy in hands and feet, mild sore throat possibly related to mucositis, and mild confusion while he was febrile. Due to initial leukocytosis, the patient remained on hydroxyurea. His total leukocyte counts and blast percentage initially increased but started to steadily decrease 7 days after the initiation of dichloroacetate. The treatment was discontinued due to a transfer to another facility for potential enrollment in an acute myeloid leukemia specific clinical trial.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

The following references are cited herein:
1. Sekeres M A et al. 2012. *Journal of clinical oncology*. Vol. 30: 4061-3.
2. Emadi A. et al. 2010. *Blood reviews*. Vol. 24: 191-9.

What is claimed is:

1. A method of treating leukemia in a subject, comprising the steps of:
   administering to said subject a therapeutically effective amount of dichloroacetate and arsenic trioxide, thereby treating the leukemia.

2. The method of claim 1, wherein said leukemia is acute myeloid leukemia.

3. The method of claim 2, wherein said acute myeloid leukemia is relapsed or refractory acute myeloid leukemia.

4. The method of claim 1, wherein said subject has a FLT3-ITD mutation.

5. The method of claim 1, wherein said dichloroacetate and arsenic trioxide are administered simultaneously or sequentially in a synergistic combination, wherein the combination has a more than additive effect.

6. The method of claim 1, wherein said dichloroacetate is administered in a concentration of about 5 mg/kg to about 50 mg/kg of the subject's body weight daily.

7. The method of claim 1, wherein said arsenic trioxide is administered in a concentration of about 0.1 mg/kg to about 0.2 mg/kg of the subject's body weight daily.

8. The method of claim 1, wherein said dichloroacetate and/or arsenic trioxide is administered orally or intravenously.

9. The method of claim 1, wherein said patient is first treated with dichloroacetate and then subsequently treated with dichloroacetate and arsenic trioxide.

10. The method of claim 9, wherein said first treatment with dichloroacetate is administered for a period of time of 24-48 hours.

11. The method of claim 9, wherein said dichloroacetate is administered at a sub-therapeutic dose.

12. A method of treating leukemia in a subject, comprising the steps of:
   administering to said subject a therapeutically effective amount of dichloroacetate for 24-48 hours; and
   administering to said subject a therapeutically effective amount of dichloroacetate and arsenic trioxide, thereby treating the leukemia.

13. The method of claim 12, wherein said leukemia is acute myeloid leukemia.

14. The method of claim 12, wherein said dichloroacetate is administered in a concentration of about 5 mg/kg to about 50 mg/kg of the subject's body weight daily and said arsenic trioxide is administered in a concentration of about 0.1 mg/kg to about 0.2 mg/kg of the subject's body weight daily.

\* \* \* \* \*